United States Patent [19]

Marchant

[11] Patent Number: 5,455,040

[45] Date of Patent: * Oct. 3, 1995

[54] ANTICOAGULANT PLASMA POLYMER-MODIFIED SUBSTRATE

[75] Inventor: Roger E. Marchant, Cleveland, Ohio

[73] Assignee: Case Western Reserve University, Cleveland, Ohio

[ * ] Notice: The portion of the term of this patent subsequent to May 12, 2009 has been disclaimed.

[21] Appl. No.: 978,205

[22] Filed: Nov. 19, 1992

Related U.S. Application Data

[63] Continuation-in-part of Ser. No. 557,740, Jul. 26, 1990, Pat. No. 5,112,457.

[51] Int. Cl.$^6$ ................................ A61F 2/02; A61F 2/06; H05F 3/00
[52] U.S. Cl. ...................... 424/426; 424/423; 514/772.2; 514/772.3; 514/822; 523/112; 523/113; 623/1; 204/165
[58] Field of Search ..................................... 424/423, 426; 514/772.2, 772.3, 822; 523/112, 113; 623/1

[56] References Cited

U.S. PATENT DOCUMENTS

| | | | |
|---|---|---|---|
| 4,685,900 | 8/1987 | Honard et al. | 604/4 |
| 5,013,306 | 5/1991 | Solomon et al. | 523/112 |
| 5,049,403 | 9/1991 | Larm et al. | 427/2.1 |
| 5,112,457 | 5/1992 | Marchant | 525/337 |

Primary Examiner—Gollamudi S. Kishore
Assistant Examiner—Carlos Azpuru
Attorney, Agent, or Firm—Calfee Halter & Griswold

[57] ABSTRACT

The present invention provides a method for surface modifying a substrate, such as an implant, to provide the substrate with anticoagulant activity and resistance to the deposition of plasma proteins; and the resulting substrate. The surface of the substrate is modified by first depositing a film of a plasma polymer such as plasma polymerized N-vinyl-2-pyrrolidone or allyl alochol on the surface of the substrate. Optionally, a neutral hydrophilic spacer molecule is attached to the plasma polymer. An anticoagulant, such as heparin, is attached either directly to the substrate or indirectly to the substrate via attatchment to the spacer molecule, when such spacer molecule is present.

10 Claims, 4 Drawing Sheets

ANTICOAGULANT PLASMA POLYMER-MODIFIED SUBSTRATE

CROSS REFERENCE TO RELATED APPLICATIONS

This application is a continuation-in-part of Ser. No. 557,740, filed Jul. 26, 1990, now U.S. Pat. No. 5,112,457, issued May 12, 1992.

BACKGROUND OF THE INVENTION

The use of synthetic biomaterials to sustain, augment or completely replace diseased human organs has increased tremendously over the past thirty years. Synthetic implants have cardiovascular applications such as vascular grafts, heart valves, and ventricular assist devices; extracorporeal systems; and a wide range of invasive treatment and diagnostic systems. Unfortunately, existing biomaterials suffer from problems associated with surface-induced thrombosis, or clot formation, such as thrombotic occlusion and thromboemboli, and infection. Synthetic vascular grafts having a diameter less than 6 mm are currently impracticable, because of potential thrombotic occlusion, and clinical experience with the artificial heart has been plagued with problems of thromboemboli and infection. Advances in the development of artificial organs and artificial vascular grafts have resulted in the need for nonthrombogenic materials.

Thrombosis is initiated by the deposition of a plasma protein layer on the surface of the implanted biomaterial. Thereafter, platelets, fibrin, and possibly leukocytes, adhere to the deposited protein. The interactions between the plasma proteins and the surface of the implant determine the adhesion, activation and spreading of platelets, the activation of coagulation, cell attachment and protein deposition.

There have been several attempts to create nonthrombogenic surfaces on polymer implants thereby increasing the blood-biocompatibility of implants.

Early attempts included precoating the implants with proteins not involved in thrombosis, such as albumin, to mask the thrombogenic surface of the implant. However, such implants loose their nonthrombogenic properties within a short time. Attempts have been made to mask the thrombogenic surface by coating gelatin onto implants such as ventricular assist devices. While the gelatin coating reduced the thrombi, it did not prevent thromboemboli and infection.

Attempts have been made to render implants nonthrombogenic by coating the surface of the implant with polyethylene oxide to mask the thrombogenic surface of the implant. While this reduced thrombogenisis, the coupling of polyethylene oxide to the surface of the implant involves very complex procedures.

There have also been attempts to prepare nonthombogenic surfaces by attaching heparin to biomaterials; heparin was selected because of heparin's potent anticoagulant properties. Such attempts required that the surface of the implant be first modified by the attachment of a coupling molecule before heparin can be attached. For example, the positively charged coupling agent tridodecylmethylammonium chloride, is coated onto an implant, which provides a positively charged surface and allows heparin, which has a high negative charge density, to be attached. However, the heparin slowly dissociates from the surface, to expose the positively charged, TDMAC surface which is particularly thrombogenic. The TDMAC attracts platelets and other cells; cells surfaces have a high negative charge density. Thus the TDMAC heparin coated implant is successful only for short term implants such as catheters.

Implants coated with heparin coupled to coupling molecules typically have limited anti-thrombogenic effectiveness because commercial heparin preparations contain many heparin molecules which having no anticoagulant activity. Moreover, the surfaces soon become covered by adsorbing protein on exposure to blood, thus neutralizing the anticoagulant activity of the active heparin molecule.

It is desirable to have implants which resist plasma protein deposition and which demonstrate anticoagulant activity. Nonthrombogenic implants would reduce the need for aggressive anticoagulant therapy, improve the performance of implants, particularly cardiovascular prosthetic devices, and encourage the development of devices not currently feasible.

SUMMARY OF THE INVENTION

The present invention provides a method for surface modifying a substrate, such as an implant, to provide the substrate with anticoagulant activity and resistance to the deposition of plasma proteins, thereby reducing the thrombogenicity of the implant. The invention also relates to the resulting structure. The surface of the substrate is modified by first depositing a film of a plasma generated polymer on the surface of the substrate. Optionally, a neutral hydrophilic spacer molecule is attached to the plasma polymer. An anticoagulant, such as heparin, is attatched either directly to the substrate or indirectly to the substrate via attachment to the spacer molecule, when such spacer molecule is present.

DETAILED DESCRIPTION OF THE INVENTION

According to the present invention, biomaterials which resist protein deposition, and have anticoagulant activity, and a method for making such biomaterials, are provided. The surface of the substrate, such as polyethylene, is modified by plasma polymerizing polar organic monomers onto the surface of the substrate to provide a film of a plasma generated polymer on the surface. Preferably, a neutral hydrophilic spacer molecule is attached to the plasma polymer. An anticoagulant is ether directly attached to the plasma polymer film, or, preferably, is indirectly attached via the spacer molecule, when such spacer molecule is present, to the plasma polymer film. The anticoagulant, such as, for example, heparin, preferably a polysaccharide or oligosaccharide of heparin, preferably having a high affinity for antithrombin III. (As used herein, the term polysaccharide encompasses oligosaccharide.) The method is surface specific and enhances the biocompatibility of biomedical substrates without adversely affecting the desirable bulk properties of the biomaterial.

The Substrate

The substrate is any material demonstrating suitable biocompatability, such as, for example polyethylene. Other suitable materials include, for example: polyesters, for example: Dacron®, carbon into pyrolytic carbon; polycarbonate; polymer membranes, for example, cellulose acetate, polyacrylonitrile; fluorocarbon polymers, for example Teflon®, Impra® and Gortex®; polysulfones; polyvinly chloride; silicone rubber for example, Silastic® from Dow Corning; silicone polymers; polypropylene; polyurethanes; nonpolymeric materials such as metals, for example, titanium, silicone, glass; and, mixtures or composites thereof. The selection of the substrate material depends upon the mechanical and functional properties required for the implant.

The Plasma Polymerized Film

Monomers which may be plasma polymerized so as to provide a plasma polymer film that is covalently bound to the substrate, and which will provide a plasma polymer film which will bind to either the anticoagulant or to a spacer molecule that binds the anticoagulant, are suitable. As used herein, "plasma polymer film" means a plasma generated polymer film, which provides functional groups for the attachment of the anticoagulant or the spacer molecule. Suitable monomers include N-vinyl-2-pyrrolidone (NVP) available from Aldrich Chemical Company, Milwaukee, Wis., and allyl alcohol from Aldrich Chemical Company, both of which produced polymer films that adhere to the substrate. The formation of the plasma polymer film is generally independent of the substrate material and is surface specific, so that the methodology described herein could be adapted to modify the surfaces of substrates composed other biomaterials, in addition to PE, regardless of composition. The plasma polymerization enhances the biocompatibility of the substrate without adversely affecting the desirable bulk properties of the substrate. Where the substrate is nonpolymeric, it is preferred that a base layer of polyhexamethyldisilazane film be first applied to the substrate and then the plasma generated polymer film be applied to the polyhexamethyldisilazane, to provide the plasma polymer film with better adhesion to the substrate. While the polyhexamethyldisilazane is applied to the substrate by plasma polymerization the term "plasma polymer film" does not include the polyhexamethyldisilazane film.

The Spacer Molecule

The spacer molecule serves not only to promote the binding of the anticoagulant to the plasma polymer, but also to provide a solvated surface for the implant and lifts the attached anticoagulant off the surface of the substrate. However, depending on the anticoagulant, the surface may be suitably solvated so as not to require a spacer molecule. Suitable spacer molecules include, for example, 3-aminopropyltriethoxysilane ("APTS") and amino-terminated poly(ethyleneoxide) ("N-PEO").

The Anticoagulant

The anticoagulant is a molecule which possess some anticoagulant activity. Suitable anticoagulants include, for example, heparin, preferably polysaccharides of heparin.

Preparation of Plasma Polymer Modified Substrate

EXAMPLE 1

Radiofrequency (RF) plasma synthesis (glow discharge) was used to generate thin, less than 100 nm, plasma polymerized films on the NHLBI Primary Reference low density polyethylene, (PE), according to the methods contained in U.S. Pat. No. 5,112,457 which is incorporated by reference herein. The PE is ethylene oxide sterilized, 8.25 cm×2.7 cm×0.28 mm sheets, from Abiomed Inc, Danvers, MA. The RF plasma system is composed of a cylindrical flow-through Pyrex reaction chamber having a wavelength of 55 cm, and an internal diameter of 7.5 cm, which is inductively coupled to 13.56M Hz RF power source from RF Plasma Products; a monomer/gas inlet system; and a vacuum system, to provide a vacuum during the entire plasma polymerization reaction.

The argon and monomer were introduced into the reaction chamber by a stainless steel monomer inlet system. The reaction pressure was continuously monitored and maintained throughout the period of plasma reaction. The reaction chamber was coupled to the radio frequency supply by an induction coil with seven turns and about 10 mm between each turn. Fine metering valves from Nupro Company and a mass flow meter from Unit Instruments were used to control and measure the argon flow rate. Monomer flow rates were controlled by fine metering valves and measured from the pressure change during specific time period with valve to vacuum pump closed. This system is also described in Marchant, R. E., et. al., "Preparation and characterization of plasma polymerized N-vinyl-2-pyrrolidone films," *J. Polym. Sci., Polym. Chem.*, 27, 881–895 (1989) and Yu D., et al., "Formation of hydroxyl groups in plasma polymerized N-vinyl-2-pyrrolidone by reduction with sodium borohydride," *Macromolecules*, 22, 2957–2961 (1989). The PE sheets were sonicated in methanol for 15 minutes, air-dried in a class 100 clean hood and then placed into the reaction chamber along with a germanium internal reflection element which was subsequently used for infrared analysis. The sample substrates were supported in the reaction chamber by cleaned glass slides mounted on a glass rod tray. Ultra high purity grade argon, from Air Products, Inc., was used for purging the reactor, and for a plasma pretreatment consisting of a 5 minutes argon glow discharge carried out at 60 watts net input power, 0.03 torr pressure and gas flow rate of 3.0 cm$^3$ (STP)/minute. The plasma polymerization reactions were performed for 5 minutes at 25 watts net input power, a reaction pressure of 0.03 torr, an inlet monomer flow rate of 0.22 cm$^3$ (STP)/minute. These deposition conditions yielded 80–100 nm thick films of PPNVP determined by ellipsometry measurements of films deposited on silicone After polymer film deposition, the chamber was evacuated to a pressure of 3×10$^{-3}$ torr, typically for one hour, to remove possible residues. Then the chamber was purged with argon and then raised to atmospheric pressure with argon.

Both the plasma polymerized NVP (PPNVP) and the plasma polymerized allyl alcohol (PPAA) films contain hydroxyl groups, about 1–2 mmol/g, and carbonyl groups. The carbonyl groups were converted to hydroxyl groups by interfacial reduction using aqueous an 0.26M $NaBH_4$, according to methods of D. Yu, et al., described in "Formation of hydroxyl groups in plasma polymerized N-vinyl-2-pyrrolidone by reduction with sodium borohydride," *Macromolecules*, 22, 2957–2961 (1989). The plasma polymer film was placed onto a glass slide for support then placed in water. The reducing agent $NaBH_4$ was added under an argon purge to a concentration of 0.26M and stirred for 24 hours. The film was removed and rinsed with acetone. The hydroxylated plasma polymers on PE were washed three times with distilled water, left stirring in distilled water for 10 hours, then air-dried in a class 100 clean hood and stored in a desiccator.

To couple the spacer molecule amino-terminated poly-(ethylene oxide) (N-PEO) on to the PPNVP, the hydroxylated samples were first washed with distilled water, and then with acetone:water (30:70, v/v), and acetone:water (60:40, v/v) solutions. The samples were then transferred to a stirred, ice-cold, acetone:water (60:40, v/v) solution, and then 0.5 ml of freshly prepared 1-cyano-4-dimethlamino-pryidinium tetrafluoroborate (CDAP) in acetonitrile having a concentration of 0.1 g/ml, was added. The CDAP activates the hydroxyl groups on the PPNVP so that the N-PEO may be coupled to the hydroxyl groups on other PPNVP. After 1 minute, about 0.3–0.5 ml of a catalyst, in 0.2M triethylamine solution, was added over 1–2 minute period, which was followed by the addition 120 ml of ice-cold 0.05N HCl. The solution was allowed to stand for 15 minutes, after which, the polymer samples were retrieved and washed briefly with cold distilled water, and 20 mM phosphate buffer saline (PBS) solution having a pH of 7.0. The activated samples were placed immediately in small bottles containing 0.2 g/ml N-PEO, having a molecular weight of about 2000 from $Sp^2$ Scientific Polymer Products, Ontario, N.Y., in PBS. The coupling reaction of the NPEO to the PPNVP was carried out by rocking the bottles on an aliquot mixer for 24 hours at 4° C. to provide PPNVP-NPEO The samples were washed repeatedly with distilled water and then air dried in a clean hood and stored in a desiccator.

EXAMPLE 2

For coupling the PPNVP-PE samples to the APTS spacer molecule, the hydroxylated samples were prepared as in Example 1, then immersed for 2 hours in an anhydrous solution of 0.15 ml/ml APTS, from Aldrich Chemical Company, in benzene. The samples were then washed repeatedly with acetone and with distilled water, air dried in a clean hood and stored in a desiccator.

EXAMPLE 3

Plasma polymerized films of allyl alcohol on polyethylene were prepared as in Example 1, except that allyl alcohol was used instead of the NVP, and the inlet monomer flow rate was 0.5 $cm^3$ (STP)/minute. The PPAA films were about 120–140 nm thick. The resulting product in which the P-NEO spacer molecule is attached to the PPAA is designated PPAA-PNEO and was prepared as in Example 1.

EXAMPLE 4

Plasma polymerized films of allyl alcohol on polyethylene were prepared as in Example 3. The APTS was coupled to the PPAA by immersing the hydroxylated samples in an anhydrous solution of 0.15 ml/ml APTS in benzene, to provide PPAA-APTS. The samples were then repeatedly washed with acetone and distilled water, air dried in a clean hood and stored in a desiccator.

EXAMPLE 5

A plasma generated polymer film of hexamethyldisilazane was generated on nonpolymeric substrates, such as glass and germanium crystals, to provide a base layer and promote the adhesion of the PPNVP polymer film, according to the plasma polymerization method in example 1. However, liquid nitrogen, rather than dry ice and acetone, was used to degass the monomers before the initial argon treatment. The plasma polymerization for the hexamethyldisilazane lasted about 12 to 15 seconds, to provide a 3–5 nm thick film.

Characterization of Plasma Polymer Modified Polyethylene

Infared Analysis

The surface-modification of the PE by the deposition of the plasma polymer film was characterized by fourier transform infrared spectroscopy using the attenuated total reflectance (FTIR-ATR) technique. Infrared analysis of untreated PE, plasma polymer modified PE, and of plasma polymer films deposited directly on germanium, were carried out using a Digilab FTS-40 FTIR spectrometer equipped with an ATR accessory from Wilkes Scientific, and a liquid nitrogen cooled MCT detector. A germanium internal reflection element with dimensions of 50×20×2 mm and nominal incidence angle of 45° was used with the ATR accessory. Spectra were obtained by co-adding 1024 interferogram scans obtained at a resolution of 8 $cm^{-1}$. Absorbance spectra were obtained by ratioing the single beam spectra with the single beam spectra of the cleaned germanium crystal. To obtain absorbance spectra of plasma polymerized films on PE, spectral subtraction techniques were used to eliminate the contribution of the PE, after the spectra were normalized to the (C—H) peak at 1466 $cm^{-1}$ in untreated PE.

The infrared analysis confirmed the formation of plasma polymer films on the PE; the completion of the derivatization reaction; and the coupling of the spacer molecule to the plasma polymer films. The treatment of PE with argon glow-discharge plasma leads to electron impact dissociation of surface hydrogens, which in turn generates free radical sites in the plasma polymer surface as well as the formation of unsaturated carbon-carbon bonds. The latter result is seen in the IR spectra of FIGS. 1–4 as an out-of-plane bending vibration, (C—H), in trans vinyl, located at 960 $cm^{-1}$. The monomers, NVP and allyl alcohol, also undergo electron impact dissociation in the non-equilibrium plasma environment generating free radicals. The dissociated monomer diffuses to the surface of the PE and combines with surface free radicals to provide a covalently-bound polar polymer film.

Figure 1:
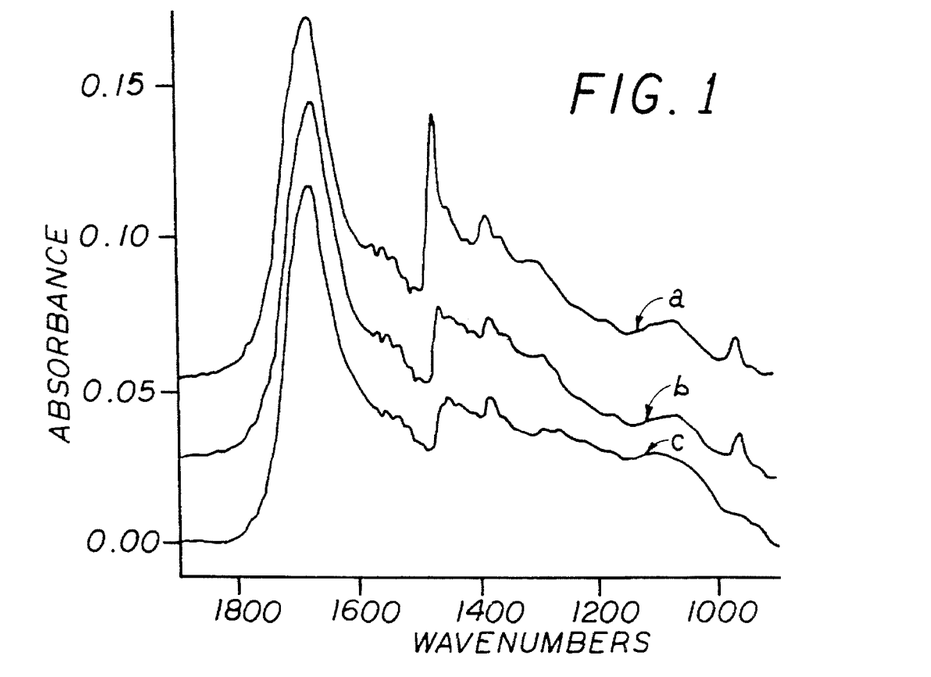
FIG. 1. ATR-FTIR spectra, 1900–1000 $cm^{-1}$ region, of: (A) PPNVP on PE; (B) PPNVP on PE, where the contribution from PE was removed by digital subtraction; and (C) PPNVP on germanium.

FIG. 1 shows three ATR-FTIR spectra (1800–900 $cm^{-1}$ region) of: spectra (a) PPNVP on PE; spectra (b) PPNVP on PE after digital subtraction of the untreated PE; and, spectra (c) PPNVP on germanium. The close similarity between spectra B and C demonstrates that the spectral subtraction emphasizes the thin film, 80–100 nm, PPNVP component of the surface region. There are only minor differences between spectra of the plasma polymerized films deposited directly on germanium as compared to the films deposited on PE. However, since untreated PE was used as the reference for digital subtraction, the analysis did not take into account the contribution of the argon treatment. The effect was observed in subtracted spectra by the presence of the trans vinyl absorption band at 960 $cm^{-1}$.

Figure 2:
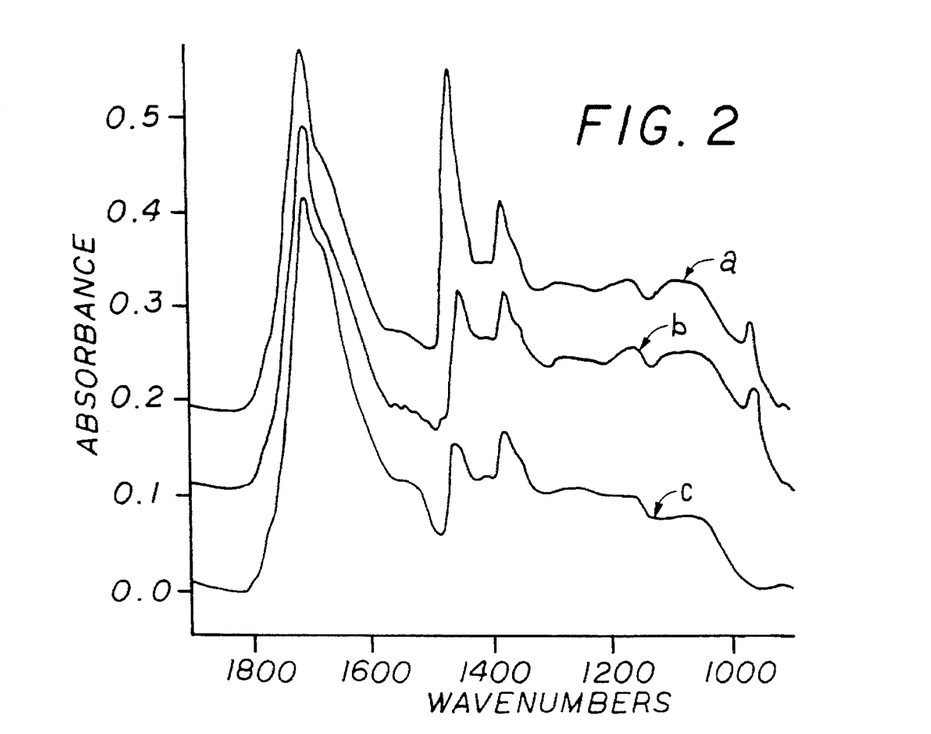
FIG. 2. ATR-FTIR spectra, 1900–1000 $cm^{-1}$ region, of: (A) PPAA on PE; (B) PPAA on PE, where the contribution from PE was removed by digital subtraction; and (C) PPAA on germaniume FIG. 3. ATR-FTIR spectra, 1900–1000 $cm^{-1}$ region, of: (A) PPNVP on PE; (B) PPNVP on PE reduced by aqueous sodium borohydride; and (C) amine terminated polyethylene oxide (PEO-N) coupled to reduced PPNVP on PE.

A possible effect of the electron impact dissociation on the monomer structure is the loss of desired functional groups during the polymerization. Such effect may depend upon the functional group, the monomer structure and RF plasma deposition conditions. Under the discharge conditions employed, a significant loss of hydroxyl groups was observed for the PPAA compared to the monomer allyl alcohol. Spectra of PPAA on PE, PPAA on PE after digital subtraction, and PE on germanium, are shown in FIG. 2. The carbonyl groups that are formed in the PPAA films and in the PPNVP films, were subsequently reduced by chemical derivatization to obtain the desired hydroxyl groups, which are apparent at about 1080 $cm^{-1}$, $v(C-O(H))$.

Figure 3:
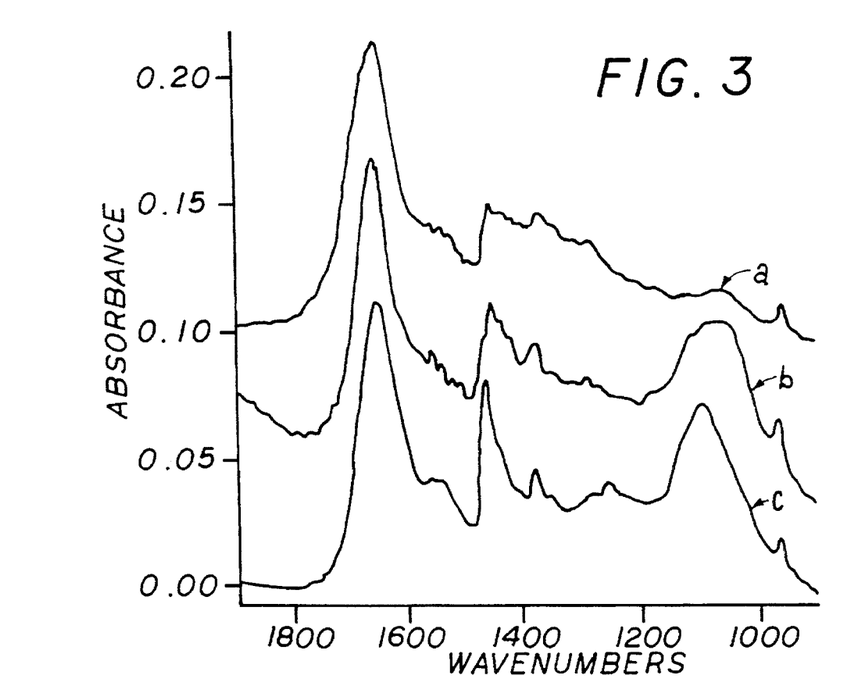

FIG. 3 is an IR spectra of PPNVP on PE, the product of interfacial reduction following conversion of carbonyl to hydroxyl groups, and the subsequent coupling reaction to N-PEO. Hydroxyl groups were identified in the reduced PPNVP by in relative increase of $v(C-O-)H$, in hydroxyl at 1150–980 $cm^{-1}$, and a relative decrease in the intensity and band width of $v(C=O)$ at 1670 $cm^{-1}$. FIG. 3, spectra c, confirmed the presence of PEO on the surface of PE as indicated by a shift in the band position of the $v(CO)$; evidence for the presence of the amine comes from the $v(C-N)$ at 1250 $cm^{-1}$ and $\delta(N-H)$ at 1550 $cm^{-1}$.

Figure 4:
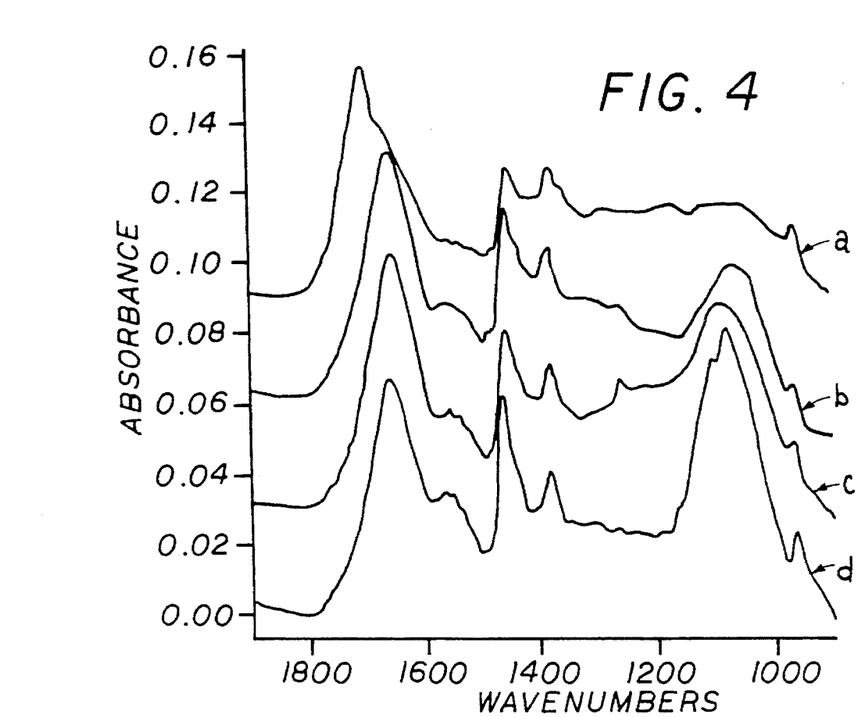
FIG. 4. ATR-FTIR spectra 1900–900 $cm^{-1}$ spectral region, of: (A) PPAA on PE; (B) PPAA on PE reduced by aqueous sodium borohydride; (C) amine terminated polyethylene oxide (PEO-N) coupled to reduced PPAA on PE; and (D) 3-aminopropyltriethoxysilane (APTS) coupled to reduced PPAA on PE.
Figure 5:
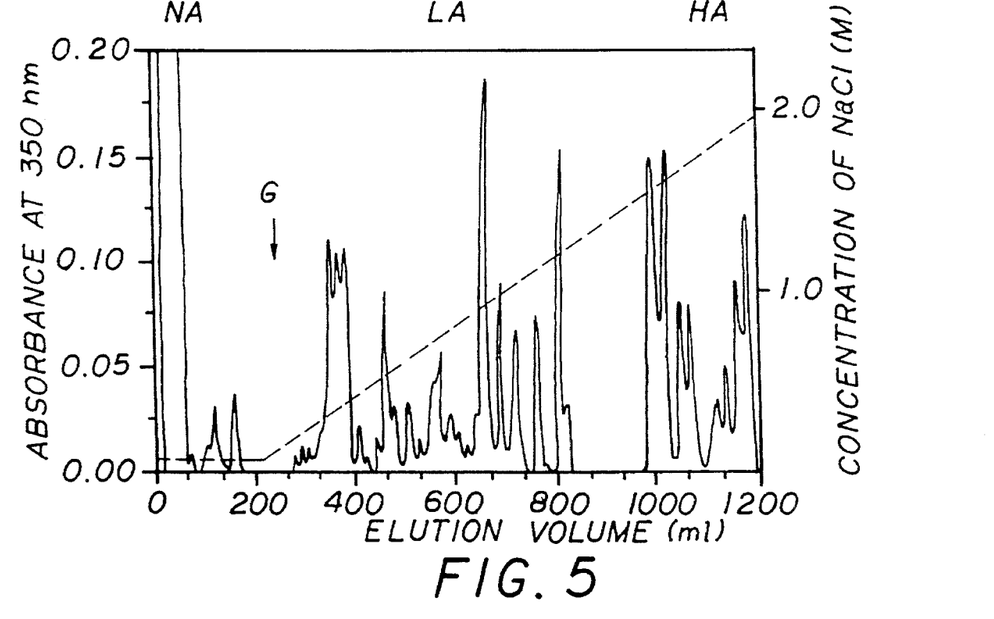
FIG. 5. Affinity chromatography separation of heparin polysaccharides on antithrombin III agrose column. Approximate positions of the non-adsorbed fraction (NA), low affinity fraction (LA) and high affinity fraction (HA) are indicated.

FIG. 4 shows the same group of spectra as FIG. 3 but for PPAA on PE, and has a spectra for PPAA-PE with APTS. The spectral changes were comparable with those for PPNVP. However, there was a marked spectral shift in the carbonyl peak after reduction. This difference may be attributed to the presence of reducible carbonyl groups, possibly keto or aldehyde groups, in the PPAA, which were not present in significant concentrations in PPNVP. Spectra D in FIG. 4, is of the reduced PPAA-APTS film. Spectra D has two strong overlapping peaks at 1100 $cm^{-1}$ and 1070 $cm^{-1}$, which are attributed to $v(C-O)$ and $v(Si-O)$ in the APTS; such peaks are not present in Spectra B of FIG. 4.

ESCA Analysis

Surface analysis of the reduced PPAA was performed using a Perkin Elmer PHI-5400 ESCA system with a 400 W magnesium X-ray source at 44.74 pass energy and 45° take off angle. The ESCA result confirmed the presence of 2.9 atomic percent silicon after coupling APTS to the reduced PPAA.

Preparation of the Anticoagulant

Heparin is a structurally heterogeneous, highly sulfated glycosaminoglycan, consisting of an alternating glycine-serine protein core t with polysaccharide side chains composed of alternating 1→4 linked residues of uronic acid (L-glucuronic and D-glucuronic acids) and glucoasamine attached to the serine residues by a tetrasaccharide linkage region. The anticoagulant activity of heparin is due to its ability to greatly accelerate, by 2–3 orders of magnitude, the rate at which antithrombin III (ATIII) inactivates serine proteases of the coagulation system, including thrombin and factor Xa. Heparin dissociates after the ATIII-protease complex has formed, so that the catalytic action of a single heparin molecule is capable of accelerating the formation of multiple ATIII-protease complexes. A unique pentasaccharide sequence, containing 3-0 and a 6-0 sulfated glucosamine residues, is essential for the binding-induced conformational change in ATIII.

The protein core of heparin was removed because it has no anticoagulant activity and its presence on the surface of the substrate would reduce entropic repulsive force and increase the adsorption of plasma proteins.

First, an aqueous solution of crude heparin having an average MW 5,000–25,000, derived from porcine intestinal mucosa, was obtained from Sigma Chemical Co. St Louis, Mo. The crude heparin and 10.0 mg/ml sodium salt solution was passed through a 3×8 cm cation exchange column containing 200–400 mesh Dowex 50W-X8 H+resin and washed with about 100 ml water. The pH was monitored during the ion exchange. The elutate was then mixed with 250 ml ethylene glycol dimethyl ether and cooled to −10° C. using an ice-salt bath. Partial deaminative cleavage of crude heparin was carried out by the addition of 10 ml isopentyl-nitrite. The reaction was quenched after 40 minutes by adjusting the pH to 8.0 with 2.0M Tris buffer. The mixture was concentrated by vacuum distillation at 37° C., and desalted by passage through an Amicon 8400 ultrafiltration membrane having a 500 molecular weight cutoff, from Diaflo Ultrafilters Company. Next, 5 ml saturated aqueous sodium acetate solution was added to 20 ml of the mixture and poured immediately into 2 liters of stirred cold 95% ethanol. The heparin polysaccharide precipitated and was collected on a glass filter having a pore size 0.45 μm and washed with 95% ethanol. The resulting heparin polysaccharide was a mixture of polysaccharides having varying affinities for ATIII (hereinafter referred to as "mixed affinity heparin"). This mixed affinity heparin possesses a terminal aldehyde group on the terminal 2-5 anhydromanose unit.

High affinity heparin, that is heparin polysaccharides having a high affinity for ATIII, was prepared as above, but before reductive amination, 170 ml of the cleaved heparin was dissolved in 10 ml of aqueous buffer containing 50 mMNaCl and 50 mM Tris-HCl at pH of 7.4. The cleaved heparin solution was applied to an 3×37 cm affinity column containing antithrombin III-agarose, fro Sigma Chemical Company. The column was equilibrated with the same buffer. The heparin solution was washed through the column with the buffer, and the non-adsorbed heparin fraction was eluted. A 3 m NaCl linear salt gradient elution of increasing ionic strength was then used to obtain the polysaccharide fractions with increasing affinity for ATIII. The concentration of polysaccharide in elutant fractions was analyzed for uronic acid by the carbazole reaction, standardized with known amount of 2-glucuronolactone and using a 33% uronic acid content in the polysaccharides according to Bitter, T. et. al., "A Modified Uronic Acid Carbazole Reaction", *Anal. Biochem.*, 4, 330–334 (1962). The collected fractions were pooled to provide three different fractions: non-adsorbed heparin (NA-heparin), low affinity heparin (LA-heparin) and high-affinity heparin (HA-heparin). The fractions were then concentrated and desalted on an Amico 8400 ultrafiltration membrane system having a 1000 molecular weight cut-off. The heparin polysaccharide was then desalted and lyophilized.

Anticoagulant Activity and Binding of the Anticoagulant

The anticoagulant activities of the crude heparin and the affinity separated polysaccharide heparin fractions were measured by commercial chromogenic assays for the inhibition of factor Xa and thrombin, enzymes necessary for the coagulation of blood. The commercial assays are available from Kabi Vitrum in Columbus, Ohio. The heparin was analyzed as a complex consisting of the heparin sample and added purified ATIII. The crude heparin and the polysaccharide heparin samples were incubated with an excess of bovine factor Xa, which was neutralized in proportion to the concentration of active heparin-ATIII complex present. The remaining factor Xa then catalysed the cleavage of p-nitroaniline (pNA) from the commercial chromogenic substrate S-2222. The amount of pNA that was released was measured photometrically at 405 nm after quenching the reaction with 20% acetic acid. The correlation between the absorbance and the heparin concentration was linear between the range of 0.1–0.7 IU/mL, and this assay was used to estimate the anticoagulant activity of the HA-heparin attached to the substrate. Untreated polyethylene samples were used as reference blanks for the assay. A similar procedure using a commercial assay from Kabi Vitrum containing the chromogenic substrate S2238 was used for the determination of thrombin inhibition for solution samples.

The anti-factor Xa activity, thrombin activity, uronic acid content, and percent recovery for the pooled fractions are shown in Table I.

TABLE I

Properties of Crude Heparin and Heparin Polysaccharide Fractions

| Heparin | Factor Xa Inhibition (IU/mg) | Factor IIa Inhibition (IU/mg) | Uronic Acid Content (% dry weight) | Yield (% recovery from crude) |
|---|---|---|---|---|
| Crude Heparin | 138 ± 20 | 111 ± 7 | 30.3 | — |
| Non-Adsorbed | 93 ± 15 | 36 ± 1 | 25.2* | 61.6 |
| Low Affinity | 64 ± 36 | 16 ± 10 | 29.2 | 24.1 |
| High Affinity | 592 ± 120 | 182 ± 34 | 32.3 | 14.3 | n = 3, ± standard deviation. Estimated errors for the uronic acid content = ±1%.
*Protein content in the nonadsorbed fraction was estimated to be 9.45 ± 1%, as measured by Pierce micro BCA assay.
— no data available
IU-international units The HA-heparin showed an approximately 5 fold increase in anti-factor Xa activity, as compared to the crude heparin. However, the HA-heparin showed only a marginal increase in thrombin inhibition. Significant inhibition of thrombin requires a minimum polysaccharide molecular weight of approximately 5400 Daltons, equivalent to 18 monosaccharide units. The high affinity heparin fraction included polysaccharides of heparin that have a molecular weight below 5400. These polysaccharides demonstrate a high anti-factor Xa activity, but low anti-thrombin activity, thereby lowering the average antithrombin activity of the fraction. The difference in the functional properties among the three fractions results from distinct structural differences of the heparin polysaccharide molecules. The non-adsorbed heparin fraction, which has an anti-factor Xa activity of 93 IU/mg consists of: a protein core (-Gly-Ser-)n; a linkage region containing D-glucuronic acid, two D-galactose and D-xylose residues; and some short sequences of oligosaccharides that may be retained on this linkage region. Some of the molecules contain the unique pentasaccharide sequence for binding ATIII. However, the structural feature of heparin required for the heparin to bind to ATIII and to exhibit anticoagulant activity is a unique pentasaccharide sequence. The pentasaccharide sequence is present on the heparin molecules in the HA-heparin fraction. The HA-heparin fraction had an anti-factor Xa activity of 592 IU/mg.

Molecular Weight of the HA-Heparin

The molecular weight distribution of the HA-heparin fraction was estimated by gel chromatography using a 2.5×92 cm Sephadex G-75 column, and an elution solvent containing 20 mM Tris, 50 mM NaCl, having a pH 7.0. at a flow rate of 2.0 m/minute Linear dextrans having molecular weights of: 39,100; 19,600; 11,000; 8,000 and 5,000 from Sigma Chemical Company, were used as reference molecular weight standards, with analysis of the uronic acid content as determined by the carbazole reaction. Bitter, T. et. al., "A Modified Uronic Acid Carbazole Reaction" *Anal. Biochem.*, 4, 330–334 (1962). A calibration curve of KaV values against log molecular weight was calculated for the standards, which was then used to estimate the molecular weight of the HA-heparin.

Figure 6:
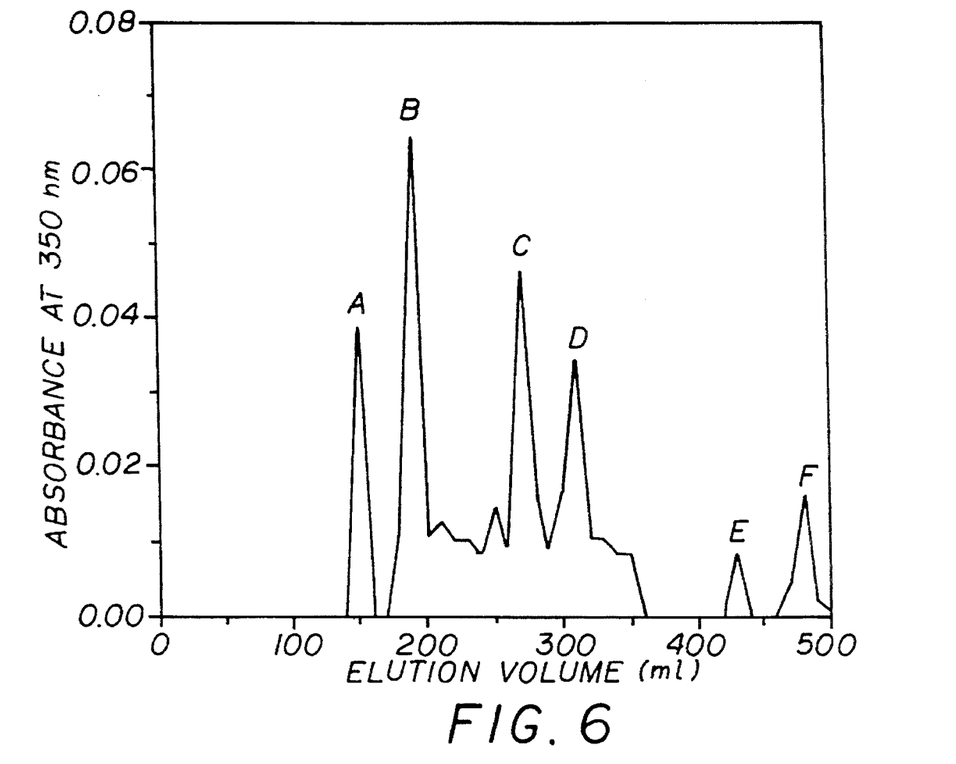
FIG. 6. Molecular weight distribution of high affinity heparin on Sephadex G-75 column by measuring uronic acid content.

Based on the calibration curve derived from dextran standards, the average molecular weight of the HA-heparin is about 17,500. The molecular weight distribution of HA-heparin, as determined by uronic acid content, is shown in FIG. 6. Molecular weights and calculated Kav values for the eluted HA-heparin fractions are listed in Table II.

TABLE II

Molecular Weights of Polysaccharide Fractions in HA-heparin[a]

| Sample | $K_{av}$[b] | Molecular Weight[c] (Weight average) |
|---|---|---|
| Dextran Standards | | |
| 1 | 0.00 | 39,100 |
| 2 | 0.288 | 19,600 |
| 3 | 0.582 | 11,000 |
| 4 | 0.673 | 8,000 |
| 5 | 1.00 | 5,000 |
| HA-heparin Fractions | | |
| A | 0.00 | >39,100 |
| B | 0.063 | 33,400 |
| C | 0.38 | 16,200 |
| D | 0.54 | 11,300 |
| E,F | | <5,000 |

[a]:Molecular weights determined on Sephadex G-75 column
[b]:KaV is defined as (Ve − Vo)/(Vt − Vo), where Ve = elution volume, Vo = void volume, Vt = column volume.
[c]:Molecular weights were determined by comparing the KaV values with those of dextran standards of known molecular weight.

Attachment of HA-Heparin Polysaccharides to the substrate

The plasma polymer modified PE and the untreated PE were cut into 5 mm diameter disks using a biopsy punch and then washed with distilled water. Six polymer disks were prepared from each of the plasma polymer modified PE samples from Examples 1–4 and untreated PE samples. Each disk was immersed in an aqueous solution containing 0.2–0.4 mg/ml HA-heparin, to which 0.40.6 mg/ml sodium cyanoborohydride was added for a final concentration of sodium cyanoborohydride of 1.9 mg/ml. The vials were then placed on a rocker for 24 hours, after which, the disks were washed repeatedly with PBS buffer having a pH 7.0 and distilled water, and stored under distilled water. It is believed that the aldehyde on the reducing terminal 2-5 anhydromannose unit of the HA-heparin was reductively aminated with the terminal amino group on either the NPEO or the APTS which were coupled to the plasma polymer modified PE.

For control experiments, the HA-heparin was adsorbed from the aqueous solution onto untreated PE and onto PE samples surfacemodified by plasma polymerization. The samples were then washed by the same procedure employed for immobilized samples.

Analysis of HA-heparin Bound to the Substrate

The anticoagulant activities of the HA-heparin bound to plasma polymer modified PE were measured by the chromogenic assay for the inhibition of factor Xa. Based on this measurement, the anticoagulant activity for the bound heparin was estimated to be 30–70 mIU/cm$^2$, with binding estimated to be 56–119 ng/cm$^2$, as shown in Table III.

Sulfur content on the surface of samples was measured by ESCA using a Perkin Elmer PHI5400 ESCA system with a magnesium x-ray source. Surface sulfur was determined using a take-off angle of 45°, and binding energies were referenced to the hydrocarbon C1s core level peak centered at 285.0 eV. The results are shown in Table III.

TABLE III

Activity and Sulfur Content of HA-Heparin on Bound to the Substrate

| Substrate | Factor Xa (mIU/cm$^2$) | Inhibition (ng/cm$^2$) | Sulfur (atomic %) |
|---|---|---|---|
| PE-PPNVP-PEO-HA Heparin | 68 ± 3 | 114.8 ± 0.1 | 1.1 ± 0.3 |
| PE-PPAA-PEO-HA Heparin | 38 ± 5 | 64.8 ± 0.1 | — |
| PE-PPAA-APTS-HA Heparin | 45 ± 2 | 76.2 ± 0.1 | 1.3 ± 0.1 | n = 3, ± standard deviation
surface sulfur content was measured by ESCA.
— data not available Control samples of untreated PE exhibited negligible anti-factor Xa activity, and no surface sulfur was detected by ESCA analysis The highest anticoagulant activity, 68 mIU/cm$^2$, for bound HA-heparin was obtained with the HA-heparin bound to PPNVP-PE with a PEO spacer molecule. The next highest anticoagulant activity was obtained for PPAA film on PE with APTS spacer molecule. The sulfur content, as determined by ESCA analysis, did not significantly differ between the HA-heparin samples.

Confirmation of the presence of, HA-heparin on the plasma polymer modified PE was also obtained using a gold bead-labeled double antibody method as described by Pankowski et al. "Morphologic characteristics of adsorbed human plasma proteins on vascular grafts and biomaterials," *J. Vasc. Surg.*, 11, 599–606 (1990). Silver enhanced gold beads, having a diameter of about 200 nm, were attached to a secondary antibody, which is directed to a primary antibody (anti-antithrombin III). The anti-antithrombin III is directed against antithrombin III. The HA-heparin plasma polymer modified PE was exposed to antithrombin III and rinsed. The heparin molecules having the pentasaccharide sequence bind the antithrombin III to form a heparin antithrombin III complex. When the complex was exposed to the beads which the anti-antithrombin III was attached, the anti-antithrombin bound to the complex. The presence of the beads was determined using scanning electron microscopy.

Figure 7:
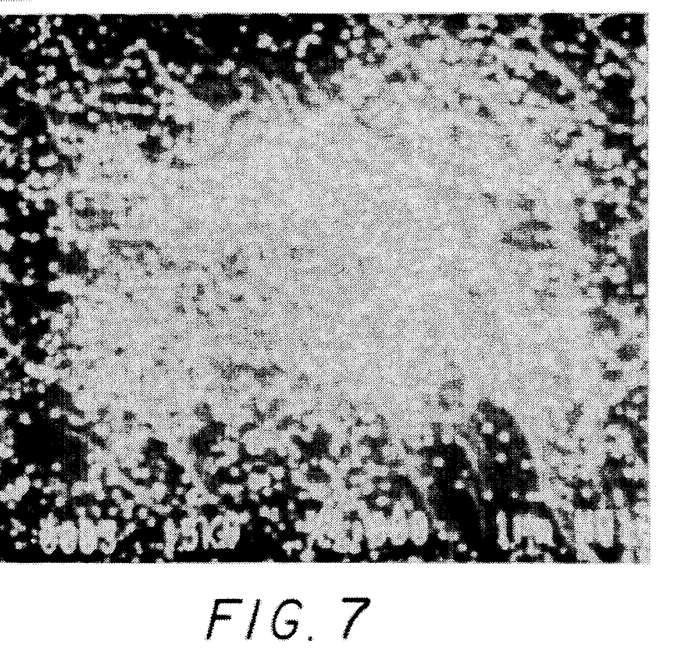
FIG. 7. SEM images (4,000×) of HA-heparin on PE which has been surface-modified by PPNVP-PEO, after labeling by an immunogold assay.
Figure 8:
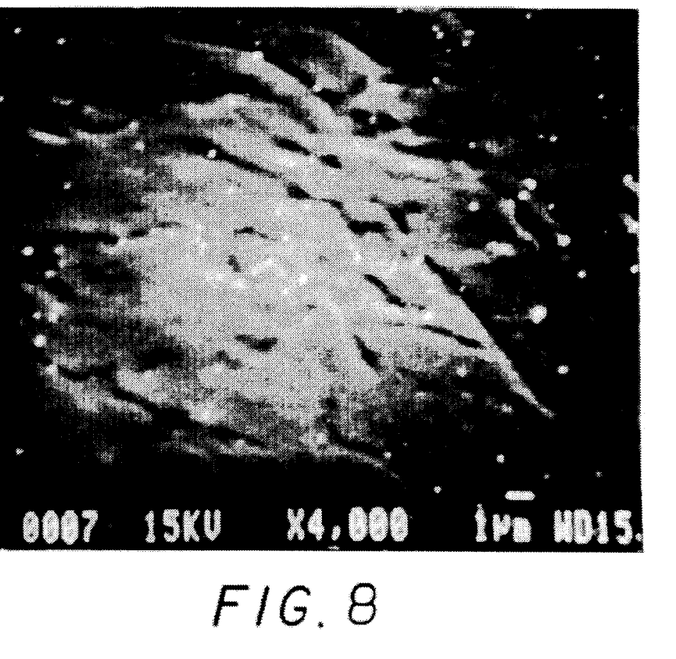
FIG. 8. SEM image (4000×) of untreated PE control.

FIG. 7 is an SEM image for HA-heparin bound to a PEO-PPNVP modified PE. From the SEM images it was determined that approximately 15% of the surface area was covered by beads, at a density of about 40×10$^7$ beads/cm$^2$, in an even distribution. In comparison, FIG. 8 shows sparse bead distribution, that is 2×10$^7$ beads/cm$^2$, which is less than 10% coverage on the the untreated PE control.

Similarly, the SEM image shown in FIG. 9 shows HA-heparin bound to PPAA-APTS modified PE having a bead densisty of 31×10$^7$ beads/cm$^2$, while the results for HA-heparin attached to the PPAA-PEO modified PE was lower at 10×10$^7$ beads/cm$^2$.

The results of the anticoagulant activity assay, that is, the Factor Xa inhibition assay, and antibody-binding assay indicated that HAheparin polysaccharides did bind to the two types of plasma polymerized PE. Some differences were observed between the PPNVP and the PPAA films as well as between the two types of spacer molecules, the APTS and the P-NEO on PPAA film. Factors that influence the coupling efficiency of the heparin polysaccharide include the concentration of hydroxyl groups in the respective plasma polymers, the degree of interfacial solvation of the plasma films by the media used during the coupling reaction, which affects functional group mobility, and the molecular weight of the heparin polysaccharide molecule to be bound.

However, the infrared results did not suggest significant differences in hydroxyl concentration for PPAA film as compared to the PPNVP film. The apparent differences in the coupling of HAheparin to the PPAA film and to the PPNVP film with the PEO spacer molecule are believed to be due to the extent of interfacial solvation which affected the PEO coupling to the PPAA. This is supported by the fact that the PPAA film exhibits a higher water contact angle, 52°±2 than the PPNVP film 35°±2, as well as lower contact angle hysteresis. The observed differences in the amount of the HA-heparin bound to the two spacer molecules on the PPAA film, probably reflects a higher binding efficiency for the small APTS spacer molecule compared with the higher molecular weight PEO spacer molecule.

The use of the HA-heparin results in the binding of relatively small molecule with high anticoagulant activity, and increases the surface density of the anticoagulant on the substrate. Polysaccharides have greater stability in vivo compared with proteins, and the anticoagulant action of heparin is catalytic, so a heparin polysaccharide-ATIII-protease complex should dissociate. In addition, bound anticoagulants are likely to provide an interface with blood that resists non-specific protein adsorption, because the polysaccharide anticoagulants are highly solvated in aqueous media such as blood.

The heparin polysaccharides in combination with RF plasma polymerization offers a methodology for coupling such biomolecules to existing clinically used substrates to provide non-thrombogenic surfaces.

Although particular embodiments of this invention has been shown and described, various adaptations and modifications can be made without departing from the scope of the invention as defined in the appended claims.

I claim:

1. A method for reducing the thrombogenicity of a substrate, comprising the steps of:

a. plasma polymerizing polar organic monomers onto the surface of the substrate to provide a plasma polymer film on the surface of the substrate;

b. attaching an a anticoagulant, so that it is bound, directly or indirectly, to the plasma polymer film to provide a substrate having reduced thrombogenicity.

2. The invention of claim 1, wherein the plasma polymer film is comprised of polymerized N-vinyl-2-pyrrolidone.

3. The invention of claim 1, wherein the plasma polymer film is comprised of polymerized allyl alcohol.

4. The invention of claim 1, wherein the anticoagulant is heparin.

5. The invention of claim 1, wherein the anticoagulant is heparin, and plasma polymer film is comprised of polymerized N-vinyl-2-pyrrolidone.

6. The invention of claim 1, wherein the anticoagulant is heparin, and the plasma polymer film is comprised of polymerized allyl alcohol.

7. The invention of claim 1, further comprising the step of attaching a spacer molecule to the plasma polymer film before the step of attaching the anticoagulant.

8. The invention of claim 7, wherein the spacer molecule is 3-aminopropyltriethoxysilane.

9. The invention of claim 7, wherein the spacer molecule is amino-terminated poly(ethyleneoxide).

10. The invention of claim 1, wherein the substrate is nonpolymeric, further comprising the step of first applying a plasma polyhexamethyldisilasane film to the substrate before the step of plasma polymermerizing the organic polar monomers onto the surface of the substrate to provide the plasma polymer film on the polyhexamethyldisilasane film.

* * * * *